(12) United States Patent
Zhao et al.

(10) Patent No.: US 11,406,134 B2
(45) Date of Patent: Aug. 9, 2022

(54) ATOMIZER AND ELECTRONIC CIGARETTE HAVING SAME

(71) Applicant: Shenzhen First Union Technology Co., Ltd., Shenzhen (CN)

(72) Inventors: Xiaoqiang Zhao, Shenzhen (CN); Renjin Wu, Shenzhen (CN); Zhongli Xu, Shenzhen (CN); Yonghai Li, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 703 days.

(21) Appl. No.: 16/374,156

(22) Filed: Apr. 3, 2019

(65) Prior Publication Data

US 2019/0307168 A1    Oct. 10, 2019

(30) Foreign Application Priority Data

Apr. 4, 2018 (CN) .......................... 201820484999.5

(51) Int. Cl.
| | | |
|---|---|---|
| *A24F 40/40* | (2020.01) | |
| *A24F 40/485* | (2020.01) | |
| *A61M 11/04* | (2006.01) | |
| *B05B 7/16* | (2006.01) | |
| *A24F 40/10* | (2020.01) | |
| *A24F 40/50* | (2020.01) | |

(52) U.S. Cl.
CPC .......... *A24F 40/485* (2020.01); *A24F 40/40* (2020.01); *A24F 40/10* (2020.01); *A24F 40/50* (2020.01); *A61M 11/042* (2014.02); *B05B 7/1686* (2013.01)

(58) Field of Classification Search
CPC ........ A24F 40/485; A24F 40/40; A24F 40/10; A24F 40/50; A61M 11/042; B05B 7/1686
See application file for complete search history.

(56) References Cited

U.S. PATENT DOCUMENTS

| | | | |
|---|---|---|---|
| 9,795,169 B1 | 10/2017 | Zhu | |
| 2006/0196518 A1* | 9/2006 | Hon | ........................ A24F 40/40 |
| | | | 131/347 |
| 2016/0157522 A1* | 6/2016 | Zhu | ........................ A24F 40/42 |
| | | | 131/329 |
| 2016/0262452 A1* | 9/2016 | Zhu | ........................ A24F 40/44 |
| 2018/0077968 A1* | 3/2018 | Qiu | ........................ A24F 40/46 |

FOREIGN PATENT DOCUMENTS

| | | |
|---|---|---|
| CN | 206 542 922 U | 10/2017 |
| EP | 3 153 199 A2 | 4/2017 |

* cited by examiner

*Primary Examiner* — Truc T Nguyen
(74) *Attorney, Agent, or Firm* — PROI Intellectual Property US; Klaus Michael Schmid

(57) ABSTRACT

An atomizer and an electronic cigarette having the same are provided, the atomizer includes a base; an adjusting ring fixed on the base and configured to adjust a volume of air inflow, the adjusting ring bored with a first air inlet; and an atomizing component partly received in the adjusting ring and being in rotatable connection with the base. Part of the atomizing component received in the adjusting ring is bored with a second air inlet corresponding to the first air inlet. When an external force drives the atomizing component excluding the part thereof received in the adjusting ring to rotate relatively to the base, an overlap ratio of the first air inlet and the second air inlet is capable to be adjusted.

18 Claims, 7 Drawing Sheets

ATOMIZER AND ELECTRONIC CIGARETTE HAVING SAME

TECHNICAL FIELD

The present disclosure relates to the field of electronic cigarettes, and particularly to an atomizer and an electronic cigarette having same.

BACKGROUND ART

The electronic cigarette is generally composed of a smoke pipe for storing tobacco liquid, an atomizer and an electronic cigarette. The atomizer is electrified by a power supply and capable of vaporizing the tobacco liquid into an aerosol mist which may simulate a feeling of smoking real tobaccos to users. Since compared with the traditional tobaccos, it has advantages of good portability, no open flame and environmental friendly, the electronic cigarette becomes a mature substitution of the real tobaccos in the market, to be a hit for extensive users.

During invention process, a problem known to the inventors: the electronic cigarettes are mostly using an adjusting ring to adjust a volume of air inflow, the adjusting ring is comparatively small, exerting a detrimental influence on operation over time.

SUMMARY

In view of the drawbacks in the prior art, the present disclosure relates to an atomizer and an electronic cigarette having the same, which are capable of adjusting the volume of air inflow.

In order to solve the above technical problem, the present disclosure provides an atomizer according to independent claim 1 whereas various embodiments of an atomizer and improvements thereto are recited in the dependent claims. An atomizer includes: a base, an adjusting ring configured to adjust a volume of air inflow and fixed on the base; the adjusting ring bored with a first air inlet; an atomizing component, partly received in the adjusting ring and being in rotatable connection with the base; as used herein, part of the atomizing component received in the adjusting ring is further provided with a second air inlet corresponding to the first air inlet; when an external force drives the atomizing component excluding the part thereof received in the adjusting ring to rotate relatively to the base, an overlap ratio of the first air inlet and the second air inlet is capable to be adjusted.

Optionally, the adjusting ring has a stopper; the atomizer includes a reservoir, a heater and an air inlet component; the air inlet component is disposed inside the adjusting ring; an end of the heater inserts into the adjusting ring to fix the air inlet component, an opposite end of the heater being protruding into the reservoir; the stopper is configured to abut against the air inlet component, permitting the air inlet component to be received in the adjusting ring; the second air inlet is disposed on the air inlet component; the heater has an air-inlet pathway, an end of the air-inlet pathway is in communication with the second air inlet.

Optionally, the stopper is provided with a through groove, the air inlet component has a limiting part disposed in the through groove and rotated relatively along the through groove; the through groove is configured to limit a rotating angle of the limiting part.

Optionally, the reservoir includes a first base, a second base and a shell; the second base is sleeved on the heater, an end of the shell is fixed on the second base, the first base is fixed with an opposite end of the shell.

Optionally, the atomizing component further includes a gas conductive pipe, an end thereof is fixedly connected with the heater, an opposite end thereof is fixedly connected with the first base.

Optionally, the atomizer further includes a circuit board and a light emitting element disposed inside the reservoir; the circuit board is fixedly connected with the air inlet component to connect the light emitting element.

Optionally, the atomizing component further includes an electrode passing through the base, the circuit board and the air inlet component to be coupled with the heater; the electrode is further coupled with the circuit board.

Optionally, the circuit board has a supporter abutting against the base and being slidably connected with the base.

Optionally, the atomizer includes a mouthpiece and a top cover, the mouthpiece is fixed with the top cover; the top cover is disposed at the top of the atomizing component.

To solve the above technical problem, an electronic cigarette is provided in accordance with another embodiment of the present disclosure, including a power supply and the aforementioned atomizer, the base of the atomizer is coupled with the power supply.

Additional aspects and advantages of the present disclosure will be: the present disclosure relates to an atomizer and an electronic cigarette having same. By fixing the adjusting ring on the base, the adjusting ring has a first air inlet, the atomizing component is inserted into the adjusting ring, the first air inlet is disposed correspondingly to the second air inlet, when the atomizing component is rotating relatively to the base, the first air inlet is rotatable with the second air inlet to adjust an overlap ratio there between further to control the volume of air inflow of the electronic cigarette, consequently controlling a volume of the aerosol without the user rotating the adjusting ring, therefore it is easy to adjust the aerosol produced by the electronic cigarette.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

With reference to FIG. 1 to FIG. 7, 1 represents an electronic cigarette, 10 represents an atomizer, 11 represents a mouthpiece; 110 represents a first air hole; 12 represents a top cover; 120 represents a second air hole; 13 represents an atomizing component; 130 represents a first air inlet; 131 represents a reservoir; 1310 represents a first receiving chamber; 1311 represents a first base; 13110 represents a connecting hole; 13111 represents a liquid inlet; 1312 represents a second base; 1313 represents a shell; 132 represents a heater; 1320 represents an air-inlet pathway; 1321 represents a heating element; 1322 represents a mediator; 1323 represents a separator; 133 represents an air inlet component; 1331 represents a limiting part; 134 represents an gas conductive pipe; 135 represents an electrode; 1351 represents an insulating ring; 14 represents a base; 15 represents an adjusting ring; 150 represents a second air inlet; 151 represents a stopper; 1510 represents a through groove; 16 represents a circuit board; 161 represents a main board; 1611 represents a connecting component; 1612 represents a controller; 162 represents a cover plate; 163 represents a rivet; 71 represents a light emitting element; 20 represents a power supply.

DETAILED DESCRIPTION

Figure 1:
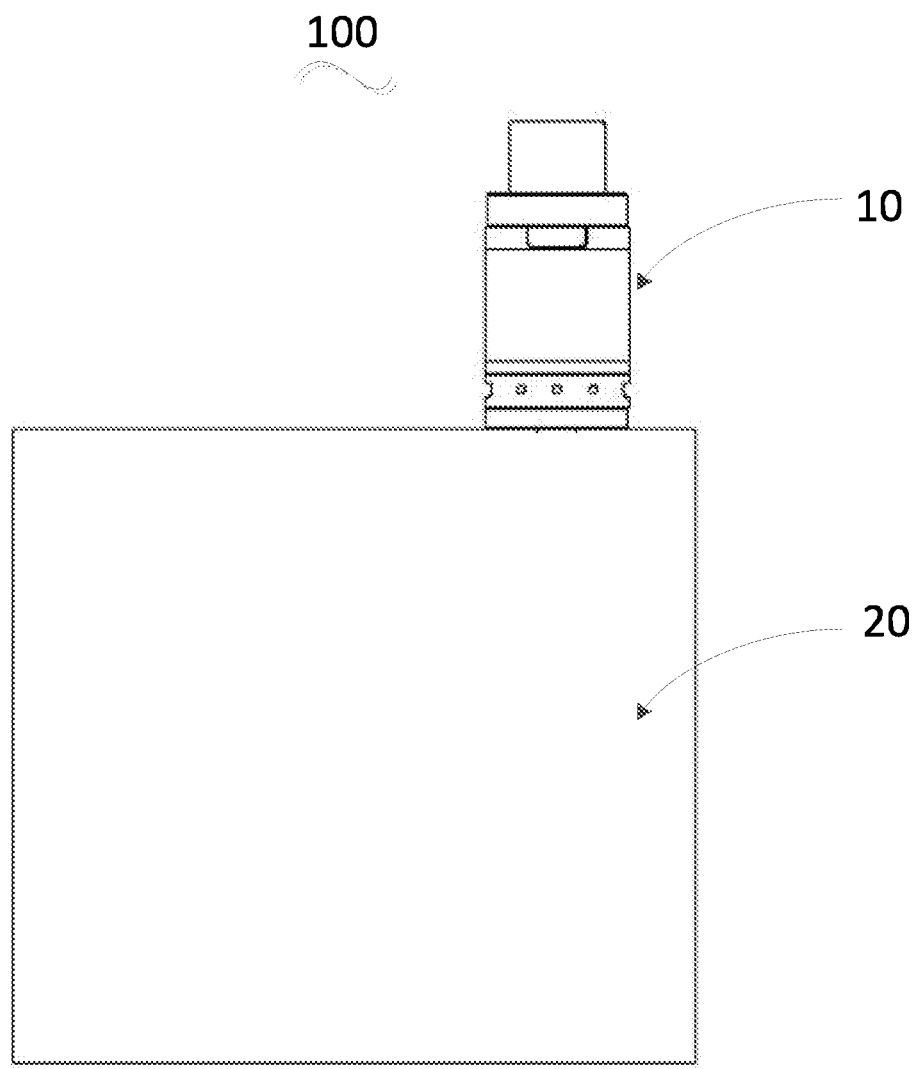
FIG. 1 is an aspect view of an electronic cigarette in accordance with an embodiment of the present disclosure.

As described herein, referring to FIG. 1, which is an aspect view of an electronic cigarette in accordance with an embodiment of the present disclosure. The electronic cigarette 1 includes an atomizer 10 and a power supply 20. The power supply 20 is coupled with the atomizer 10, the power supply 20 is configured for supplying power to the atomizer 10, permitting the atomizer 10 to heat the tobacco liquid to generate an aerosol mist.

More specifically, the power supply 20 may be detachably connected with the atomizer 10 via a thread. Of course, in some alternative embodiments, the power supply 20 may be connected with the atomizer 10 in other ways such as snap joint or rivet joint etc.

Figure 2:
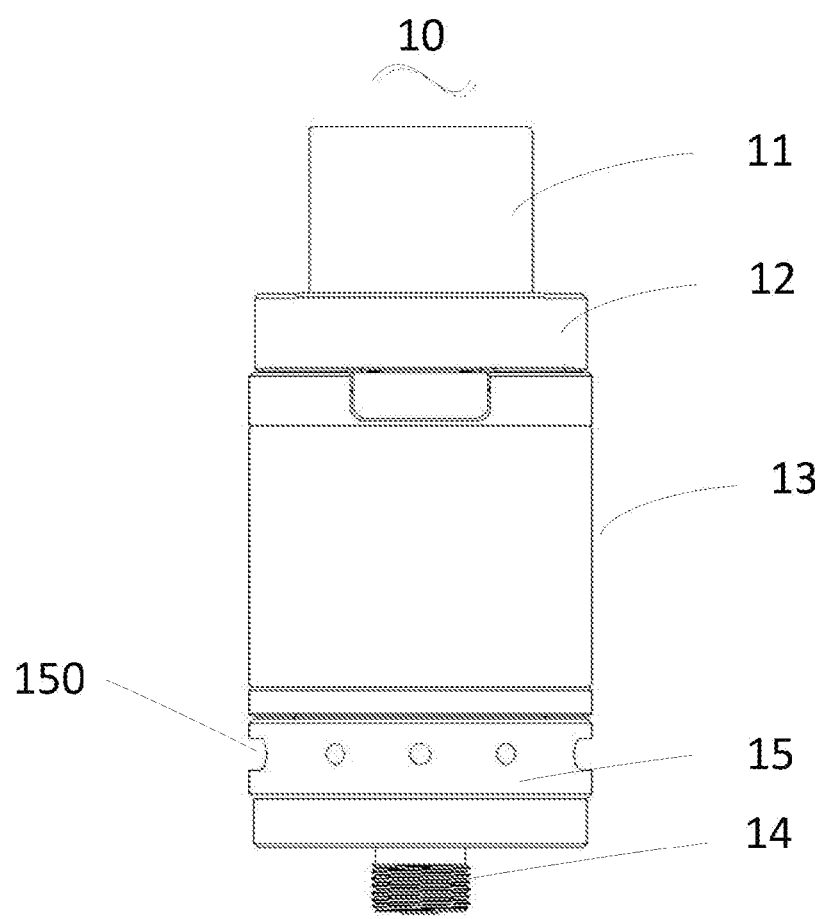
FIG. 2 is an aspect view of an atomizer in accordance with an embodiment of the present disclosure.
Figure 3:
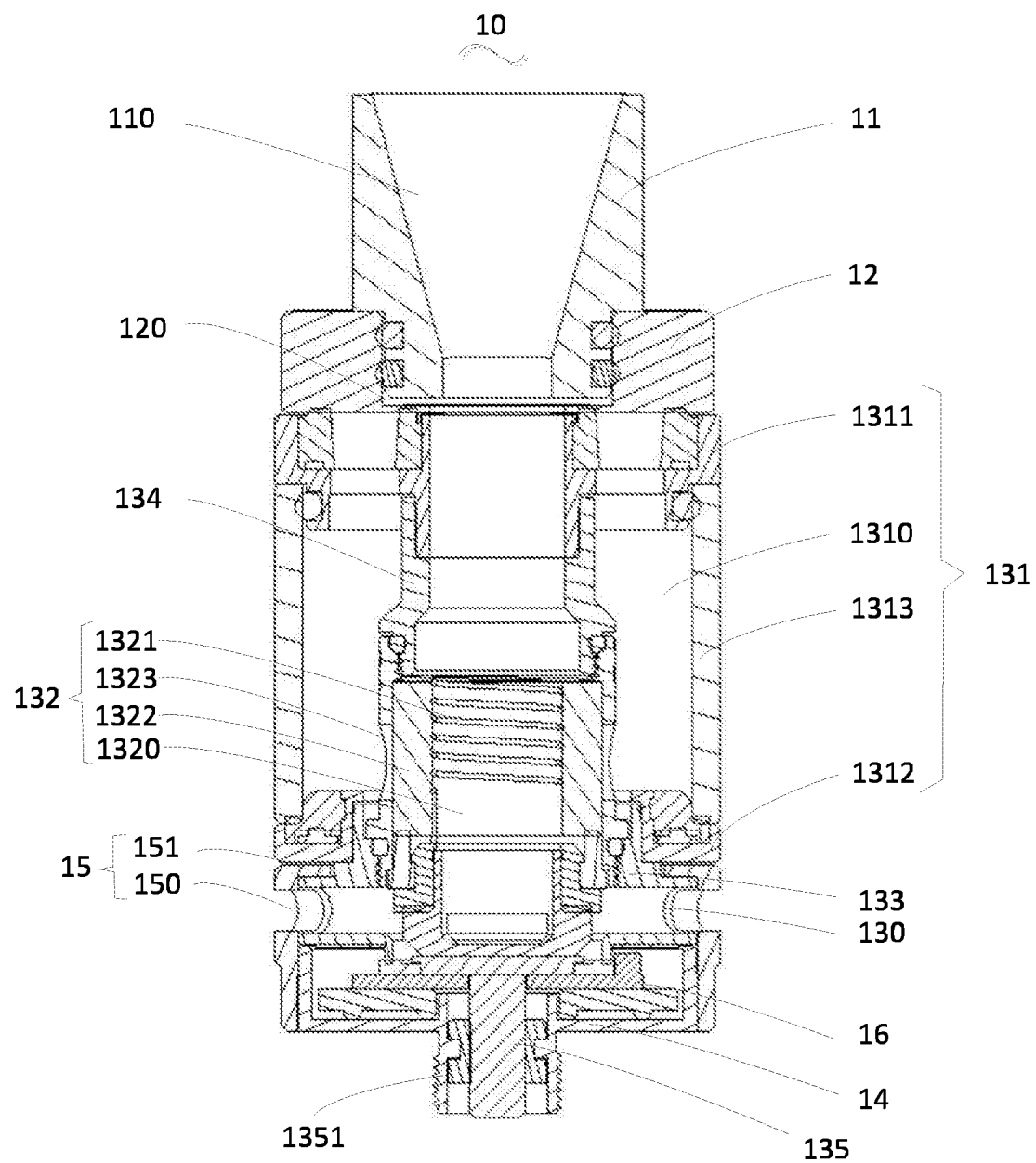
FIG. 3 is a cross-sectional view of the atomizer along a preset angle in FIG. 2.

Furthermore, reference is made to FIG. 2 and FIG. 3, which illustrate an atomizer in accordance with an embodiment of the present disclosure. The atomizer 10 includes a mouthpiece 11, a top cover 12, an atomizing component 13, a base 14, an adjusting ring 15, a circuit board 16 and a light emitting element 17.

The mouthpiece 11 is connected with a side of the top cover 12, another side of the top cover 12 is connected with an end of the atomizing component 13, part of the atomizing component 13 inserts into the adjusting ring 15 to be rotatably connected with the base 14. The adjusting ring 15 is fixedly connected with the base 14 and provided with an air inlet 150. Part of the atomizing component 13 inserting into the adjusting ring 15 is bored with a second air inlet 130 corresponding with the first air inlet 150. When an external force drives the atomizing component 13 exclusive of the part thereof received in the adjusting ring to make the atomizing component 13 relatively rotatable to the base 14, which may adjust an overlapping ratio of the first air inlet 150 and the second air inlet 130, therefore controlling the volume of air inflow.

The mouthpiece 11 is a hollow cylinder, with a first air hole 110 formed therein. The first air hole 110 has a shape of truncated cone passing through the mouthpiece 11, configured for a user to absorb the aerosol mist.

The top cover 12 is a hollow cylinder, with a second air hole 120 formed therein. The second air hole 120 is a cylindrical through hole, passing through the top cover 12, corresponding with a location of the first air hole 110. The mouthpiece 11 is detachably connected with an inner wall of the second air hole 120. The inner wall of the second air hole 120 is provided with an O-shaped gasket ring for strengthening the air tightness of the atomizer 10.

The atomizer 13 includes a reservoir 131, a heater 132, an air inlet component 133, a gas conductive pipe 134 and an electrode 135. One end of the heater 132 inserts into the adjusting ring 15 to be fixed with the air inlet component 133, the opposite end of the heater 132 passes through the reservoir 131 to be connected with the gas conductive pipe 134.

More specifically, the reservoir 131 includes a first base 1311, a second base 1312 and a shell 1313. The first base 1311 and the second base 1312 are respectively carried on two sides of the shell 1313. The shell 1313 has a first receiving chamber 1310 formed therein, the heater 132 is partly received in the first receiving chamber 1310. The first receiving chamber 1310 is configured for storing tobacco liquid, allowing the heater 132 to heat and atomize.

Figure 4:
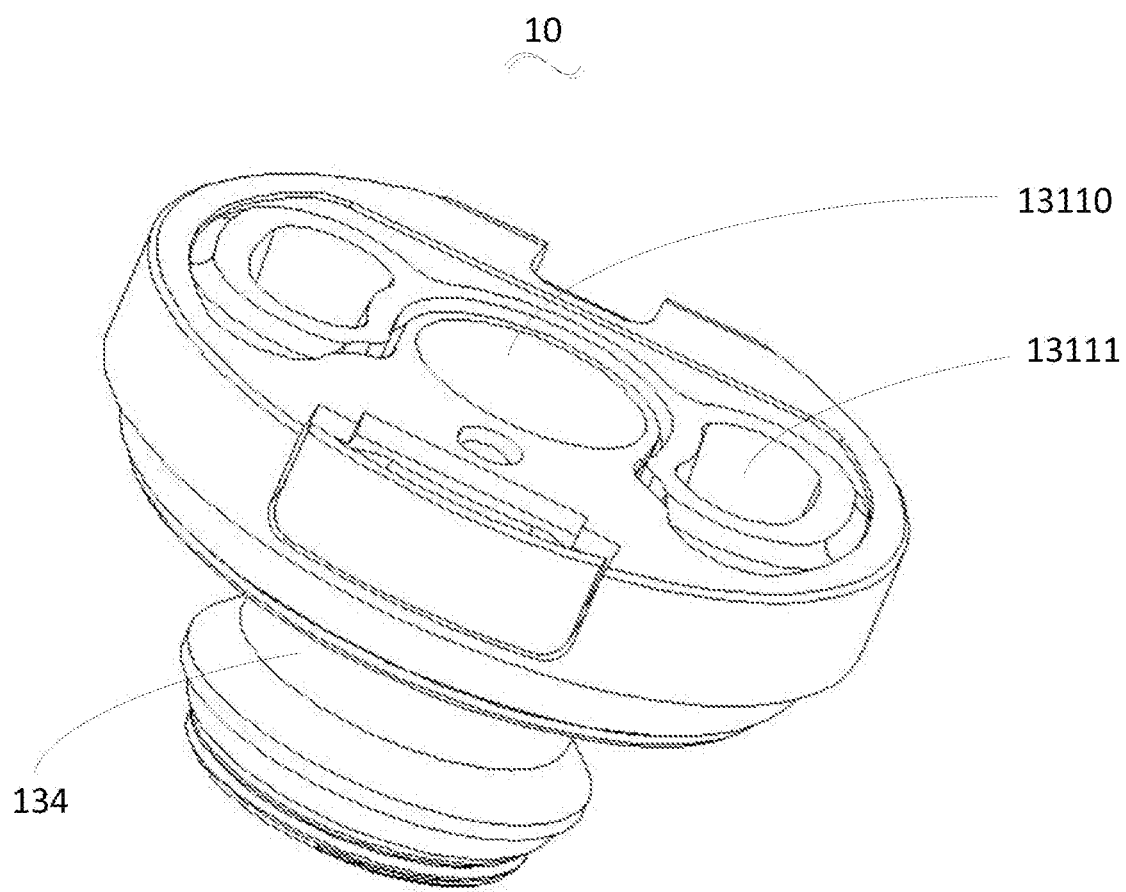
FIG. 4 is an illustrated perspective view of part of the atomizer in FIG. 2.

As used herein, referring to FIG. 4, the first base 1311 is bored with a connecting hole 13110 and a liquid inlet 13111. An end of the connecting hole 13110 is corresponding with the second air hole 120 of the top cover 12, permitting the connecting hole 13110 to intercommunicate with the first air hole 110 of the mouthpiece 11. Accordingly, the opposite end of the connecting hole 13110 is in communication with the gas conductive pipe 134. The liquid inlet 13111 is a through hole with a rectangular shape, symmetrically disposed at two sides of the second air hole 120, the number of the liquid inlet 13111 is at least one. Preferably, in the embodiment, the number of the liquid inlets 13111 is two, respectively disposed on two sides of the second air hole 120. The liquid inlet 13111 intercommunicates with the first receiving chamber 1310. The liquid inlet 13111 is configured for the user to replenish tobacco liquid to the first receiving chamber 1310 via the liquid inlet 13111, permitting the heater 132 to heat the tobacco liquid in the first receiving chamber 1310.

In the embodiment, the top cover 12 covers the first base 1311, and the top cover 12 is in flip connection with the base 1311. When the user replenishes the tobacco liquid, firstly dismantling the mouthpiece 11, then opening the top cover 12 to expose the liquid inlet 13111, injecting tobacco liquid into the liquid inlet 13111 to replenish the tobacco liquid. Of course, in some alternative embodiments, the top cover 12 is connected with the first base 13111 via other methods such as a thread screw etc.

The second base 1312 is annual-shaped to be fixedly connected with the shell 1313. The second base 1312 is provided with a groove (not shown). The light emitting element 17 is disposed in the groove.

Understandable, in other embodiments, the atomizer 13 further includes a transparent gasket ring (not shown). The transparent gasket ring is made of glass materials, or other materials, the gasket ring is not only transparent but also semi-transparent, just is capable of penetrating light. The transparent gasket ring is disposed in the groove and configured to surround the light emitting element 17 with the second base 1312, so as to strengthen water-proof property of the light emitting element 17.

The shell 1313 is made of transparent materials, such as glasses pr plastics etc., which may penetrate light also work as an aid for users to monitor the usage of the tobacco liquid. The shell 1313 is a cylindrical structure, an end of the shell 1313 is fixedly connected with the first base 1311, an opposite end of the shell 1313 is fixedly connected with the second base 1312. The shell 1313, the first base 1311 and the second base 1312 define a first receiving chamber 1310.

The heater 132 is a core of the atomizer 10 to realize heating the tobacco liquid, which includes an air-inlet pipe 1320, a heating element 1321, a mediator 1322 and a separator 1323. The mediator 1322 is disposed outside the heating element 1321; the separator 1323 is sleeved outside the mediator 1322.

As used herein, the heating element 1321 is a spiral-shaped, including an anode terminal of the heating element 1321 and a cathode terminal (not shown) of the heating element 1321. As used herein, the anode terminal of the heating element 1321 works as an anode terminal of the heater 132, the cathode terminal of the heating element 1321 works as a cathode terminal of the heater 132. The anode terminal of the heating element 1321 and the cathode terminal of the heating element 1321 are respectively coupled with the anode terminal and the cathode terminal of the power supply 20 via the base 14, to be electrified for heating.

Of course, in some alternative embodiments, the heating element 1321 may be grid-shaped, mesh-shaped, or combinations of grid-shaped and mesh-shaped.

The mediator 1322 may be made of at least one or two selected from a group of cotton fibers, polypropylene fibers, polyester fibers, nylon fibers and porous ceramics. The mediator 1322 is configured to absorb the liquid in the first receiving chamber 1310, permitting the heating element to heat the tobacco liquid absorbed by the mediator 1322.

The separator 1323 is bored with liquid conductive holes (not shown). The number of the liquid conductive holes is four, the liquid conductive hole is configured for the liquid in the first receiving chamber 1310 to flow into the mediator 1322. The separator 1323 has an end to be fixedly connected with the gas conductive pipe 134, permitting the aerosol mist generated by the heating element 1321 heating tobacco liquid to flow into the gas conductive pipe 134. An opposite end of the separator 1323 is passing through the second base 1312 to be connected with the air inlet component 133.

The separator 1323, a mediator 1322 and the heating element 1321 define an air-inlet pathway 1320, an end of the air-inlet pathway 1320 intercommunicates the second air inlet 130. The opposite end of the air-inlet pathway 1320 is disposed inside the reservoir 131. The air-inlet pathway 1320 allows the air to flow in from the second air hole 130, further pass through the mediator 1322 and the heating element 1321 to the gas conductive pipe 134.

Understandable, in some embodiments, the heater 132 may be multiple, the heater 132 may be parallel with each other, coupled to increase the aerosol mist generated.

In the embodiment, the tobacco liquid is absorbed by the mediator 1322 from the liquid conductive holes of the separator 1323. The heating element 1321 heats the mediator 1322 to generate the aerosol mist flowing into the gas conductive pipe 134. The aerosol mist may be drawn by the user from the connecting hole 13110, the second air hole 120 and the first air hole 110, later on drawn by the user from the first air hole 110 in the mouthpiece 11.

It has to illustrate, in the embodiment, sealing assembling is adopted between the separator 1323 and the gas conductive pipe 134, between the gas conductive pipe 134 and the connecting hole 13110, between the connecting hole 13110 and the second air hole 120, and between the second air hole 120 and the first air hole 110. Therefore, the air tightness of the atomizer 10 may be ensured.

The air inlet component 133 is roughly a hollow cylinder, formed inside the adjusting ring 15. An end of the separator 1323 carried on the heater 132 is passing through the adjusting ring 15 to be fixedly connected with the air inlet component 133. The opposite end of the separator 1323 is passing through the reservoir 131 to be received in the first receiving chamber 1310. The air inlet component 133 is corresponding with the base 14. The second air inlets 130 are formed on the air inlet component 133. In the embodiment, the number of the second air inlets 130 is two. The second air inlet 130 is configured for exterior air to flow into the air-inlet pathway 1320 further into the heater 132.

The gas conductive pipe 134 is a cylindrical structure, an end of the gas conductive pipe 134 is correspondingly connected with a connecting hole 13110 bored on the first base 1311; an opposite end of the gas conductive pipe 134 is fixedly connected with the heater 132.

An end of the electrode 135 is passing through the circuit board 16 and the air inlet component 133 to intercommunicate the anode terminal of the circuit board 16 and the anode terminal of the heating element 132. The opposite end of the electrode 135 is passing through the base 14 to be coupled with the anode terminal of the power supply 20. In the embodiment, the atomizer 10 has an insulating ring 1351 sleeved on an end of the electrode 135 proximal to the base 14. The insulating ring 1351 is configured to insulate the electrode 135 from the base 14.

The base 14 is roughly a hollow cylinder, an end thereof is corresponding with the air inlet component 133, an opposite end thereof is connected with the power supply 20. The base 14 is opened with a threaded screw. By relying on the threaded screw, the base 14 is coupled with the power supply 20. The base 14 and the air inlet component 133 define a second receiving chamber (not shown). The second receiving chamber is configured for receiving the circuit board 16.

Figure 5:
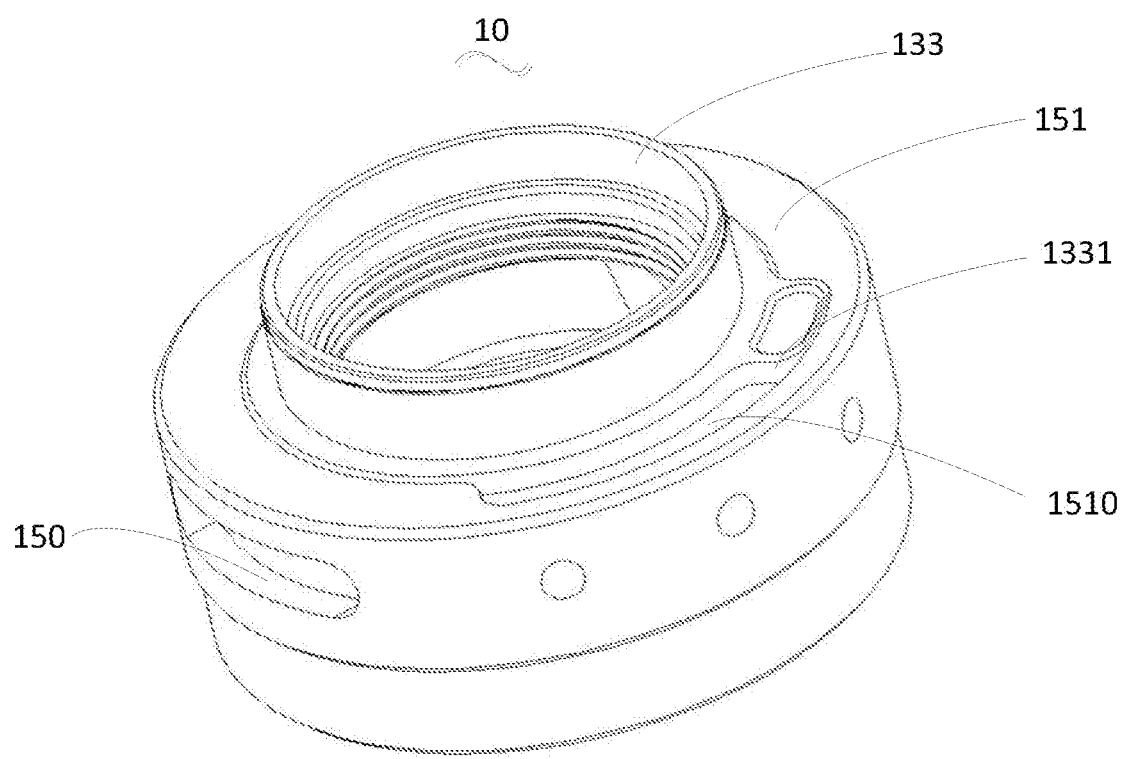
FIG. 5 is an illustrated perspective view of the part of the atomizer in FIG. 2.

Referring to FIG. 3 and FIG. 5, the adjusting ring 15 is annual, sleeved on the air inlet component 133 and the base 14 to be in contact with the air inlet component 133 and to be fixedly connected with the base 14. The adjusting ring 15 is bored with a first air inlet 150 and a stopper 151. The first air inlet 150 is rectangular, a location of the first air inlet 150 is corresponding with a location of the second air inlet 130 such that the air inlet component 133 may rotate relatively with the base 14, resulting in adjusting an overlapping ratio between the first air inlet 150 and the second air inlet 130. The exterior air flows into an overlapping area between the first air inlet 150 and the second air inlet 130 via the first air inlet 150, then entering into the heating element 1321 by through the air-inlet pathway 1320. The stopper 151 is disposed at an end of the adjusting ring 15 proximal to the second base 1312. The stopper 151 is configured for abutting against the air inlet component 133, permitting the air inlet component 133 to be received in the adjusting ring 15. When the user grasps the shell 1313 of the reservoir 131, the atomizer 10 is lifted up, in this case, the stopper 151 is abutting against the air inlet component 133 such that the base 14 is lifted up with the adjusting ring 15, resulting in a compact structure of the atomizer 10 rather than unconsolidated structure.

In the embodiment, referring to FIG. 5, the air inlet component 133 is provided with a limiting part 1331; the stopper 151 is opened with a through groove 1510; the limiting part 1331 is disposed inside the through groove 1510, making the limiting part 1331 available of rotating along the through groove 1510. The through groove 1510 is capable of confining the rotating angle of the limiting part 1331 so as to confine the angle of the atomizing component 13 rotating relatively to the base 14, which may confine the overlapping ratio between the first air inlet 150 and the second air inlet 130.

In the embodiment, when the user draws the electronic cigarette 100, the exterior air intercommunicating with the gas pathway of the atomizer 10 forms an air flowing bearing the aerosol mist generated by the heater 132, further being expelled. By relying on rotational engagement between the first air inlet 150 and the second air inlet 130, the volume of air flowing into the electronic cigarette 100 further to control the volume of the aerosol mist.

Figure 6:
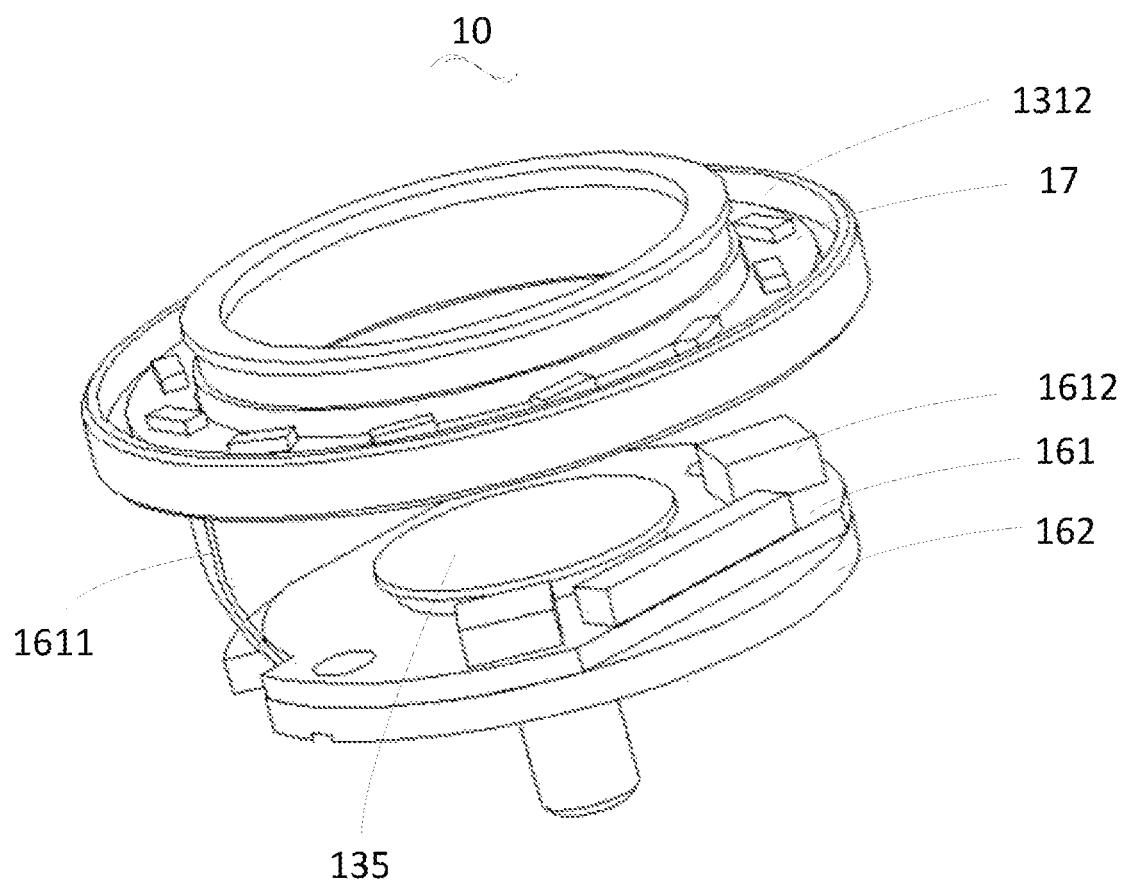
FIG. 6 is an illustrate perspective view of the part of the atomizer in FIG. 2.
Figure 7:
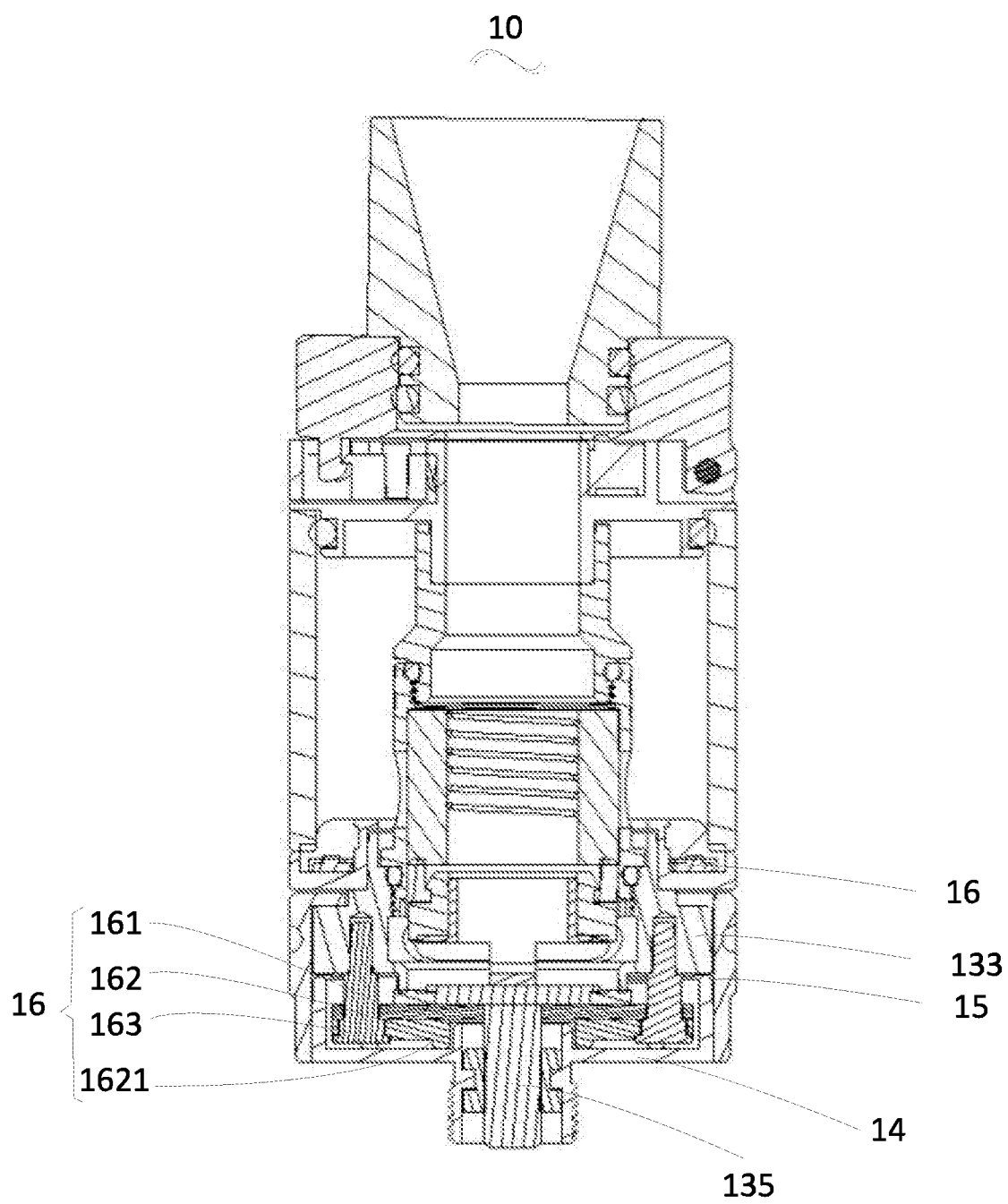
FIG. 7 is a cross-sectional view of the atomizer along another preset angle in FIG. 2.

Referring to FIG. 6 and FIG. 7, the circuit board 16 is received within the second receiving chamber, to be fixed with the air inlet component 133. When the atomizing component 13 is rotating relatively to the base 14, that means, the air inlet component 133 is rotating relatively to the base 14, the circuit board 16 would rotate along with the air inlet component 133.

The main board 161 has a connecting component 1611 and a controller 1612. The connecting component 1611 passing through the air inlet component 133 and the base 14 to be connected with the light emitting component 17 such that the light emitting component 17 is coupled with the main board 161. The controller 1612 is coupled with the light emitting component 17 via the connecting component 1611 and the controller 1612 may control the light emitting component 17 to emit light, as well as colors of the emitting light, thus control the color of the atomizer 10 appeared. The controller 1612 may control light frequencies of the light emitting component emitting, such that shimmering of the atomizer 10 is more dazzling.

The cover plate 162 works as a cathode terminal of the circuit board 16, covering the main board 161. It needs to be noticeable, the cover plate 162 does not contact with the electrode 135, while the cover plate 162 is electrically conducted with the rivets 163. The cover plate 162 has an annual supporting part 1621, well distributed on a distal side of the cover plate 162 relative to the main board 161. The supporting part 1621 abuts against the base 14 and is slidable relatively to the base 14. The supporting part 1621 may change surface-to-surface contact into line-to-surface contact, alleviating a fictional force between the cover plate 162 and the base 14, as an aid to support the circuit board 16, furthermore making the circuit board 16 rotating smoothly relatively to the base 14.

The number of the rivets 163 is two, both are disposed inside the second receiving chamber. The rivets 163 pass through the circuit board 16 to be partly inserted into the air inlet component 133. Therefore, the circuit board 16 is fixedly connected with the air inlet component 133.

In the embodiment, the rivets 163 make the cathode terminal of the circuit board 16 electrically conductive with the air inlet component 133. The cathode of the heat element 1321 passing through the second base 1312 to be electrically conducted with the air inlet component 133. The cathode of the circuit board 15 passing through the rivets 163 to be electrically conducted with the air inlet component 133. The air inlet component 133 contacts the adjusting ring 15 to be electrically conducted with the base 14. Therefore, the anode of the power supply 20 is electrically conducted with the anode of the circuit board 16 and the anode of the heating element 1321 via the electrode 135. The cathode of the power supply 20 is electrically conducted with the cathode of the circuit board 16 and the cathode of the heating element 1321 via the base 14.

Referring to FIG. 6 and FIG. 7, the light emitting element 17 is disposed inside the reservoir 131 and coupled with the circuit board 16. The light emitting element 17 may be an LED (light-emitting diode) lamp with LED chips able to evenly surround the second base 1312. When the circuit board 16 is electrified, under the control of the controller 1612, the light emitting element 17 emits lights in different colors, then, the lights penetrating through the transparent sealing rings and the shell 1313 to emit out, resulting in colors of the atomizer 10 is changeable.

In the embodiment, when assembling the atomizer 10, firstly assembling the reservoir 131, in which, firstly the mediator 1322 is sleeved on the heating element 1321 and the separator 1323 is sleeved on the mediator 1322 to assemble the heater 132; and the air conductive pipe 134 is fixed on the first base 1311, the first base 1311 is fixed with the shell 1313, an end of the separator 1323 passing through the shell 1313 is connected with the air conductive pipe 134 via a thread; the light emitting element 17 is disposed on the second base 1312; the second base 1312 is sleeved on the separator 1323 to be fixed with the shell 1313. Secondly, assembling the circuit board 16, in which, firstly the circuit board 16 is connected with the air inlet component 133 via a rivet 163; a connecting component of the circuit board 16 passing through the air inlet component 133 and the second base 1312 is connected with the light emitting component 17. Thirdly, assembling the air inlet component 133, an adjusting ring 15 and a base 14, in which, the adjusting ring 15 is sleeved on the air inlet component 133, the opposite end of the separator 1323 inserting into the adjusting ring 15 is fixed with the air inlet component 133; an end of the electrode 135 passing through the circuit board 16 is coupled with the anode of the heater 132; an opposite end of the electrode 135 is sleeved on the insulating ring 1351 to pass through the base 14; then the base 14 is fixed with the adjusting ring 15. Eventually, assembling the mouthpiece 11 and the top cover 12, in which, the top cover 12 is carried on the first base 1311 in a flip model, the mouthpiece 11 is detachably connected with an inner wall of the second air hole 120 of the top cover 12 via a threaded screw. In summary, the assembling of the atomizer 10 is finished.

In the embodiment, the atomizer 10 is coupled with the power supply 20 via the threaded screw carried on the base 14 to assemble an electronic cigarette. After the atomizer 10 is electrified with the power supply 20, the heater 132 is initiated to heat the tobacco liquid stored in the shell 1313 to generate an aerosol mist. When the user hopes to adjust a volume of the aerosol mist, one hand can grasp the power supply 20, the other hand can rotate the reservoir 131. Since the reservoir 131 is fixedly connected with the air inlet component 133, the air inlet component 133 is rotating along with the rotating of the reservoir 131. Since the adjusting ring 15 is fixed with the base 20 via the base 14, the air inlet component 133 is rotating along with the base 14. By relying on rotating engagement between the first air inlet 150 and the second air inlet 130, a volume of air flow entering into the electronic cigarette 100 is controlled so as to control the volume of the aerosol mist, without rotating the adjusting ring 15 to realize an effect of adjusting the aerosol mist.

Terminology used herein is for the purpose of describing particular embodiments only and is not intended to be limiting of the invention. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer comprising:
a base;
an adjusting ring fixed on the base and configured to adjust a volume of air inflow;
the adjusting ring bored with a first air inlet; and
an atomizing component partly received in the adjusting ring and being in rotatable connection with the base;
the atomizing component comprises a reservoir, a heater and an air inlet component which is partly received in the adjusting ring and which is fixedly connected to the reservoir; the atomizing component further comprises an air-inlet pathway, wherein a part of the air inlet component received in the adjusting ring is bored with a second air inlet corresponding to the first air inlet and an end of the air-inlet pathway is in communication with the second air inlet; the atomizing component is arranged to rotate relative to the base such that when a user grasps the atomizing component excluding the part thereof received in the adjusting ring to rotate it relatively to the base, an overlap ratio of the first air inlet and the second air inlet is capable to be adjusted.

2. The atomizer of claim 1, wherein
the adjusting ring comprises a stopper;
an end of the heater inserts into the adjusting ring to be fixed with the air inlet component, an opposite end of the heater protrudes into the reservoir;
the stopper is configured to abut against the air inlet component for permitting the air inlet component to be received in the adjusting ring;
the heater further comprises the air-inlet pathway, an end of the air-inlet pathway being in communication with the second air inlet.

3. The atomizer of claim 2, wherein
the stopper provided with a through groove, the air inlet component comprising a limit part disposed in the through groove and rotated relatively along the through groove; the through groove configured to limit a rotating angle of the limit part.

4. The atomizer of claim 2, wherein
the reservoir comprising a first base, a second base and a shell; the second base sleeved on the heater; an end of the shell fixed on the second base; an opposite end of the shell fixed on the first base.

5. The atomizer of claim 4, wherein
the atomizing component further comprising a gas conductive pipe, an end thereof fixedly connected with the heater, an opposite end thereof fixedly connected with the first base.

6. The atomizer of claim 2, wherein
the atomizing component further comprising a circuit board and a light emitting element disposed inside the reservoir; the circuit board fixed on the air inlet component to be coupled with the light emitting element.

7. The atomizer of claim 6, wherein
the atomizing component further comprises an electrode passing through the base, the circuit board and the air inlet component to be coupled with the heater; the electrode further coupled with the circuit board.

8. The atomizer of claim 6, wherein
the circuit board comprising a supporter abutting against the base and being slideably connected with the base.

9. The atomizer of claim 1, wherein
the atomizer further comprising a mouth piece and a top cover, the mouth piece fixed with the top cover; the top cover covering a top of the atomizing component.

10. An electronic cigarette comprising an atomizer, the atomizer comprising:
a base;
an adjusting ring fixed on the base and configured to adjust a volume of air inflow;
the adjusting ring bored with a first air inlet; and
an atomizing component partly received in the adjusting ring and being in rotatable connection with the base; the atomizing component comprises a reservoir, a heater and an air inlet component which is partly received in the adjusting ring and which is fixedly connected to the reservoir; the atomizing component further comprises an air-inlet pathway;

wherein a part of the air inlet component received in the adjusting ring is bored with a second air inlet corresponding to the first air inlet and an end of the air-inlet pathway is in communication with the second air inlet; the atomizing component is arranged to rotate relative to the base such that when a user grasps the atomizing component excluding the part thereof received in the adjusting ring to rotate relatively to the base, an overlap ratio of the first air inlet and the second air inlet is capable to be adjusted;

wherein the electronic cigarette further comprises a power supply coupled with the base of the atomizer and configured for supplying power to the atomizer.

11. The electronic cigarette of claim 10, wherein
the adjusting ring comprising a stopper;
an end of the heater inserts into the adjusting ring to be fixed with the air inlet component, an opposite end of the heater protrudes into the reservoir; the stopper configured to abut against the air inlet component, permitting the air inlet component to be received in the adjusting ring;
the heater further comprises the air-inlet pathway, an end of the air-inlet pathway being in communication with the second air inlet.

12. The electronic cigarette of claim 11, wherein
the stopper provided with a through groove, the air inlet component comprising a limit part disposed in the through groove and rotated relatively along the through groove; the through groove configured to limit a rotating angle of the limit part.

13. The electronic cigarette of claim 11, wherein
the reservoir comprising a first base, a second base and a shell; the second base sleeved on the heater; an end of the shell fixed on the second base; an opposite end of the shell fixed on the first base.

14. The electronic cigarette of claim 13, wherein
the atomizing component further comprising a gas conductive pipe, an end thereof fixedly connected with the heater, an opposite end thereof fixedly connected with the first base.

15. The electronic cigarette of claim 11, wherein
the atomizing component further comprising a circuit board and a light emitting element disposed inside the reservoir; the circuit board fixed on the air inlet component to be coupled with the light emitting element.

16. The electronic cigarette of claim 15, wherein
the atomizing component further comprises an electrode passing through the base, the circuit board and the air inlet component to be coupled with the heater; the electrode further coupled with the circuit board.

17. The electronic cigarette of claim 15, wherein
the circuit board comprising a supporter abutting against the base and being slidably connected with the base.

18. The electronic cigarette of claim 10, wherein
the atomizer further comprising a mouth piece and a top cover, the mouth piece fixed with the top cover; the top cover covering a top of the atomizing component.

* * * * *